US008879061B2

(12) United States Patent
Ikeda et al.

(10) Patent No.: US 8,879,061 B2
(45) Date of Patent: Nov. 4, 2014

(54) ANALYSIS APPARATUS AND ANALYSIS METHOD

(71) Applicant: Imagineering, Inc., Kobe (JP)

(72) Inventors: Yuji Ikeda, Kobe (JP); Ryoji Turuoka, Kobe (JP)

(73) Assignee: Imagineering, Inc., Kobe-shi (JP)

( * ) Notice: Subject to any disclaimer, the term of this patent is extended or adjusted under 35 U.S.C. 154(b) by 0 days.

(21) Appl. No.: 13/839,560

(22) Filed: Mar. 15, 2013

(65) Prior Publication Data

US 2013/0208275 A1   Aug. 15, 2013

Related U.S. Application Data

(63) Continuation of application No. PCT/JP2011/070774, filed on Sep. 12, 2011.

(30) Foreign Application Priority Data

Sep. 15, 2010   (JP) ................... 2010-207383

(51) Int. Cl.
   *G01J 3/30*   (2006.01)
   *G01J 3/02*   (2006.01)
   *G01N 21/68*   (2006.01)
   *G01N 21/71*   (2006.01)
   *G01J 3/443*   (2006.01)

(52) U.S. Cl.
   CPC . *G01J 3/02* (2013.01); *G01N 21/68* (2013.01); *G01N 21/718* (2013.01); *G01J 3/443* (2013.01)
   USPC ........................................ 356/316

(58) Field of Classification Search
   USPC ................................... 356/314, 318
   See application file for complete search history.

(56) References Cited

U.S. PATENT DOCUMENTS 7,821,634 B2 * 10/2010 Dillon et al. ............... 356/318
2012/0008139 A1 * 1/2012 Miziolek et al. ........... 356/318

OTHER PUBLICATIONS

Masashi Kaneko et al., "Microwave Assisted Spark Induced Breakdown Spectroscopy", Science lecture meeting of the technology car association, May 21, 2009, w/English translation, (8 pages).
International Preliminary Report on Patentability of PCT/JP2011/070774, (form PCT/IB/373) dated Mar. 19, 2013 (1 page).
Written Opinion of PCT/JP2011/070774 (form PCT/ISA/237) dated Jan. 31, 2012 (5 pages).

* cited by examiner

*Primary Examiner* — Abdullahi Nur
(74) *Attorney, Agent, or Firm* — Westerman, Hattori, Daniels & Adrian, LLP

(57) ABSTRACT

The analysis apparatus 10 includes a plasma generation device 11 and an optical analysis device 13. The plasma generation device 11 generates initial plasma by energizing a substance in space to be turned into a plasma state, and maintains the plasma state by irradiating the initial plasma with electromagnetic wave for a predetermined period of time. Then, the optical analysis device 13 analyzes the target substance 15 based on a time integral value of intensity of emission from the target substance 15 in an electromagnetic wave plasma region, which is maintained by the electromagnetic wave.

8 Claims, 10 Drawing Sheets

ANALYSIS APPARATUS AND ANALYSIS METHOD

TECHNICAL FIELD

The present invention relates to an analysis apparatus and an analysis method for analyzing a target substance by analyzing emission from plasma.

BACKGROUND ART

Conventionally, there is known an analysis apparatus and an analysis method for analyzing a target substance by analyzing emission from plasma. For example, Japanese Unexamined Patent Application, Publication No. 2010-38560 discloses an analysis apparatus of this kind.

More particularly, Japanese Unexamined Patent Application, Publication No. 2010-38560 discloses an element analysis apparatus which employs laser-induced breakdown spectroscopy. In the element analysis apparatus, laser pulses are emitted from a laser oscillator and condensed on a sample surface, thereby turning a part of the sample surface into plasma. Constituent elements of the sample surface are turned into excited state atoms. The excited state atoms emit fluorescence when transiting to a lower level. The emitted fluorescence is incident upon a fluorescence detector via an optical fiber. The fluorescence detector converts information with respect to a wavelength of the fluorescence and intensity at the wavelength into electrical signals. A computer for measurement control performs element analysis based on the resultant electrical signals.

THE DISCLOSURE OF THE INVENTION

Problems to be Solved by the Invention

In the conventional analysis apparatuses such as described above, since a laser pulse alone is employed to turn a target substance into plasma, the plasma is formed only for a short time. Therefore, integral value of intensity of emission from the plasma is not sufficient, and it has been difficult to perform analysis at a high accuracy. In order to improve accuracy of analysis, a high performance spectrometer is required.

The present invention has been made in view of the above described circumstances, and it is an object of the present invention to improve analysis accuracy of an analysis apparatus for analyzing a target substance by analyzing light (hereinafter, referred to as "plasma light") emitted from plasma.

Means for Solving the Problems

In accordance with a first aspect of the present invention, there is provided an analysis apparatus including: a plasma generation unit that generates initial plasma by energizing a substance in space to be turned into a plasma state, and maintains the substance in the plasma state by irradiating the initial plasma with electromagnetic wave for a predetermined period of time; and an optical analysis unit that analyzes a target substance based on time integral value of intensity of emission from the target substance in an electromagnetic wave plasma region, which is maintained by the electromagnetic wave.

According to the first aspect of the present invention, since the initial plasma is irradiated with the electromagnetic wave for the predetermined period of time, the plasma is maintained until immediately after the electromagnetic wave irradiation is terminated. Since it is possible to control the irradiation duration of the electromagnetic wave with ease, it is possible to control the duration of the electromagnetic wave plasma with ease. According to the first aspect of the present invention, the time integral value of intensity of the emission from the electromagnetic wave plasma, of which duration is controllable, is employed for analyzing the target substance.

In accordance with a second aspect of the present invention, in addition to the feature of the first aspect of the present invention, the plasma generation unit is controlled so that the time integral value of intensity of the emission from the electromagnetic wave plasma is greater than the time integral value of intensity of emission from the initial plasma.

In accordance with a third aspect of the present invention, in addition to the feature of the first or second aspect of the present invention, the emission from the electromagnetic wave plasma includes emission from a molecule, and the electromagnetic wave radiated from an electromagnetic wave radiation unit is adjusted in energy per unit time so that the peak of intensity of the emission from the molecule can be detected.

According to the third aspect of the present invention, the plasma light from the electromagnetic wave plasma includes emission from a molecule, the electromagnetic wave radiated from the electromagnetic wave radiation unit is adjusted in energy per unit time so that a peak of intensity of the emission from the molecule can be detected.

In accordance with a fourth aspect of the present invention, in addition to the feature of any one of the first to third aspects of the present invention, the target substance is gaseous substance or particulate substance contained in a fluid, and the optical analysis unit analyzes the target substance based on the time integral value of intensity of light acquired from a region, which is larger than a region where the initial plasma is formed, within a region where the electromagnetic wave plasma is formed.

According to the fourth aspect of the present invention, the target substance is analyzed based on the time integral value of intensity of light acquired from a region larger than the region where the initial plasma is formed, within the region where the electromagnetic wave plasma is formed. Here, in a case in which the target substance is gaseous substance or particulate substance contained in a fluid, there is concern that quantitative distribution of a specific substance is uneven depending on location. In such a case, if components in a small region are analyzed, each analysis will give a different result, and it is impossible to ensure reliability of results of analysis. Consequently, it is preferable to analyze components in a sufficiently large region. However, since the plasma is formed in a small region, if only plasma light emitted from laser plasma is analyzed, it is impossible to analyze components in a large region. On the other hand, according to the fourth aspect of the present invention, since the plasma expands due to the electromagnetic wave, it is possible to analyze light acquired from a region larger than the region where the initial plasma is formed. Therefore, the target substance is analyzed based on time integral value of intensity of light acquired from a region larger than the region where the initial plasma is formed.

In accordance with a fifth aspect of the present invention, in addition to the feature of any one of the first to fourth aspects of the present invention, at least one of energy per unit time of the electromagnetic wave radiated by the plasma generation unit and irradiation duration of the electromagnetic wave is controlled according to a phase state of the target substance.

According to the fifth aspect of the present invention, according to a phase state of the target substance, at least one of the energy per unit time of the electromagnetic wave radiated from the plasma generation unit and the irradiation duration of the electromagnetic wave is controlled.

In accordance with a sixth aspect of the present invention, in addition to the feature of any one of the first to fifth aspects of the present invention, the plasma generation unit repeats generation and extinction of the plasma at a predetermined operation cycle. The optical analysis unit analyzes the target substance based on the time integral value of intensity of the emission from the electromagnetic wave plasma each time the plasma generation unit generates plasma, and the electromagnetic wave radiated by the plasma generation unit is increased in energy per unit time in proportion to a decrease in the operation cycle.

According to the sixth aspect of the present invention, as the plasma generation unit decreases in operation cycle, the optical analysis unit, which operates in response to operation of the plasma generation unit, decreases in operation cycle. This means that the operation cycle of the analysis apparatus is decreased. In order to improve the time response of the analysis apparatus, the energy per unit time of the electromagnetic wave is required to be increased. This attributes to the fact that in order to reduce the operation cycle of the plasma generation unit, the electromagnetic wave is required to be formed for a shorter period of time. The time integral value of intensity of the emission from the electromagnetic wave plasma is decreased as the operation cycle of the plasma generation unit is decreased provided that the electromagnetic wave remains constant in energy per unit time. Therefore, according to the sixth aspect of the present invention, in order to maintain the time integral value of intensity of the emission from the electromagnetic wave plasma large even if the operation cycle of the plasma generation unit is decreased, the electromagnetic wave increases in energy per unit time in proportion to decrease in the operation cycle of the plasma generation unit.

In accordance with a seventh aspect of the present invention, in addition to the feature of any one of the first to sixth aspects of the present invention, the plasma generation unit radiates the electromagnetic wave in continuous wave form from a radiation antenna provided in a space where the initial plasma is generated during a plasma maintenance period, during which the plasma generation unit maintains the plasma.

According to the seventh aspect of the present invention, the plasma generation unit radiates the electromagnetic wave in continuous wave (CW) form during the plasma maintenance period, which is a period when the plasma is maintained by energy of the electromagnetic wave. In a plasma region, where the target substance is present, the energy of the electromagnetic wave is stably applied unlike pulsing energy of an electromagnetic wave pulse. Accordingly, it is possible to prevent occurrence of a shock wave caused by the electromagnetic wave in the plasma region during the plasma maintenance period.

In accordance with an eighth aspect of the present invention, in addition to the feature of the seventh aspect of the present invention, the target substance is moved in the electromagnetic wave plasma region during the plasma maintenance period.

In accordance with a ninth aspect of the present invention, in addition to the feature of the seventh or eighth aspect of the present invention, the plasma generation unit, upon receiving a pulse signal of constant voltage, radiates the electromagnetic wave from the radiation antenna. The optical analysis unit sets an analysis period in a constant intensity period, in which variation in intensity of emission from the plasma is equal to or less than a predetermined value, within the plasma maintenance period, and analyzes the target substance based on intensity of the emission from the plasma during the analysis period.

In accordance with a tenth aspect of the present invention, in addition to the feature of any one of the seventh to ninth aspects of the present invention, the target substance is powdery substance, and, the plasma generation unit sets power of the electromagnetic wave during the plasma maintenance period to the degree that the target substance may not scatter.

In accordance with an eleventh aspect of the present invention, in addition to the feature of the tenth aspect of the present invention, the plasma generation unit sets power of the electromagnetic wave during the plasma maintenance period to the degree that a maximum value of intensity of emission from the plasma during the plasma maintenance period is greater than the time integral value of intensity of emission from the initial plasma.

In accordance with a twelfth aspect of the present invention, in addition to the feature of anyone of the seventh to eleventh aspects of the present invention, the optical analysis unit analyzes the emission from the plasma during the plasma maintenance period, thereby detecting mixture ratios of components contained in the target substance.

In accordance with a thirteenth aspect of the present invention, in addition to the feature of anyone of the seventh to eleventh aspects of the present invention, the optical analysis unit analyzes the emission from the plasma during the plasma maintenance period, thereby detecting a temperature of gas in the electromagnetic wave plasma region.

In accordance with a fourteenth aspect of the present invention, there is provided an analysis method including: a plasma generation step of generating initial plasma by momentarily energizing a target substance to be turned into a plasma state, and maintaining the target substance in the plasma state by irradiating the initial plasma with electromagnetic wave for a predetermined period of time; and an optical analysis step of analyzing the target substance based on a time integral value of intensity of emission from an electromagnetic wave plasma, which is maintained by the electromagnetic wave.

Effect of the Invention

According to the present invention, the time integral value of intensity of the emission from the electromagnetic wave plasma, duration of which is controllable, is employed for analyzing the target substance. The electromagnetic wave plasma can be maintained longer than plasma which is formed by a laser pulse alone. Accordingly, it is possible to acquire a large value of time integral of emission intensity, thereby enabling analysis at a high accuracy without using a high performance spectrometer.

Furthermore, according to the third aspect of the present invention, since the plasma light from the electromagnetic wave plasma includes emission from a molecule, it is made possible to detect a peak of intensity of the emission from the molecule, it is possible to realize an analysis apparatus that can analyze molecules.

Furthermore, according to the fourth aspect of the present invention, since the plasma expands due to the electromagnetic wave, the target substance is analyzed based on the time integral value of intensity of light acquired from a region larger than the region where the initial plasma is formed. Accordingly, in a case in which the target substance is gaseous substance or particulate substance contained in a fluid, it is possible to realize an analysis apparatus that can analyze the target substance in a large region, which enables a highly reliable analysis when the target substance is particulate substance or gaseous substance.

Furthermore, according to the sixth aspect of the present invention, in order for the time integral value of intensity of the emission from the electromagnetic wave plasma to be large even if the operation cycle of the plasma generation unit is, the electromagnetic wave is set higher in energy per unit time as the plasma generation unit is set shorter in operation time. Accordingly, it is possible to perform analysis at a high accuracy, even if the plasma generation unit is set short in operation cycle, i.e., the analysis apparatus is set fast in time response.

Furthermore, according to the seventh aspect of the present invention, since the electromagnetic wave stably energizes the plasma region during the plasma maintenance period, it is possible to prevent occurrence of a shock wave caused by the electromagnetic wave. The analysis period, during which the optical analysis unit performs analysis, is within the plasma maintenance period. Accordingly, in a case in which the target substance is powdery substance, it is possible to prevent the target substance in the plasma region from scattering during the analysis period. Thus, it is possible to analyze the target substance in the plasma region with very little locomotion.

BEST MODE FOR CARRYING OUT THE INVENTION

In the following, a detailed description will be given of the embodiments of the present invention with reference to drawings. It should be noted that the following embodiments are mere examples that are essentially preferable, and are not intended to limit the scope of the present invention, applied field thereof, or application thereof.

First Embodiment

Figure 1:
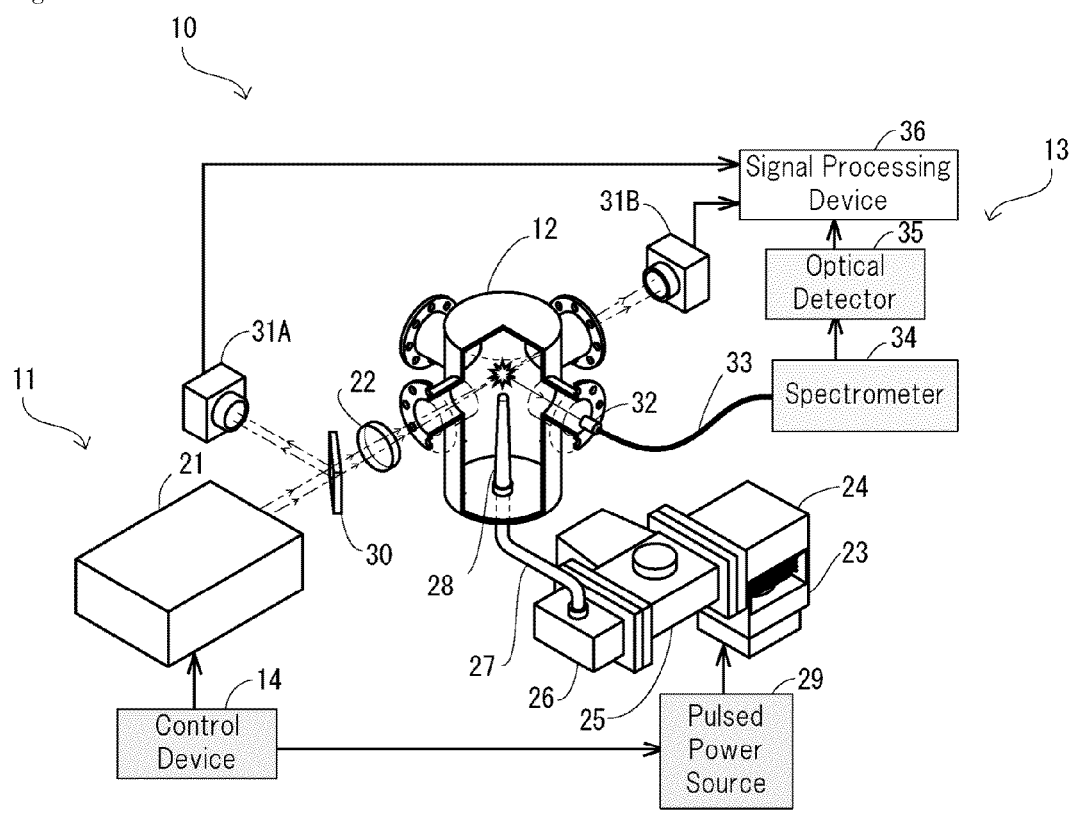
FIG. 1 is a schematic configuration diagram of an analysis apparatus according to a first embodiment.

As shown in FIG. 1, an analysis apparatus 10 according to a first embodiment is provided with a plasma generation device 11, a cavity 12, an optical analysis device 13, and a control device 14. The control device 14 controls the plasma generation device 11 and the optical analysis device 13. The analysis apparatus 10 according to the first embodiment can analyze any type of substance as a target substance regardless of whether the substance is in a state of solid, liquid, or gas, as long as the plasma generation device 11 can turn the substance into a plasma state.

Construction of Plasma Generation Device

The plasma generation device 11 includes a laser light source 21, a light collection optical system 22, a microwave oscillator 23, microwave transmission paths 24 to 27, an antenna 28, and a pulsed power source 29. The plasma generation device 11 constitutes a plasma generation unit that generates initial plasma by momentarily energizing a target substance 15 to be turned into a plasma state, and maintains the target substance 15 in the plasma state by irradiating the initial plasma with an electromagnetic wave for a predetermined period of time. The laser light source 21 and the light collection optical system 22 constitute an initial plasma generation unit that energizes the target substance 15 and turns the target substance 15 into a plasma state. The microwave oscillator 23, the microwave transmission paths 24 to 27, the antenna 28, and the pulsed power source 29 constitute a plasma maintenance unit that irradiates the initial plasma generated by the initial plasma generation unit with the electromagnetic wave for the predetermined period of time to maintain the plasma state.

The laser light source 21 oscillates a laser light, which can turn the target substance 15 into a plasma state. The laser light oscillated by the laser light source 21 passes through the light collection optical system 22 and is condensed on a focal point of the light collection optical system 22. The focal point of the light collection optical system 22 is located within the cavity 12. As the laser light source 21, for example, an Nd:YAG laser light source may be employed. As the light collection optical system 22, for example, a convex lens may be employed.

The plasma generation device 11 is configured so that energy density of the laser light condensed at the focal point of the light collection optical system 22 is not below a breakdown threshold value of the target substance 15. This means that the laser light is configured to have a sufficient power to turn the target substance 15 located at the focal point into plasma.

The microwave oscillator 23 is connected to the antenna 28 via the microwave transmission paths 24 to 27. The microwave transmission paths 24 to 27 include a waveguide 24 coupled to the microwave oscillator 23, an isolator 25 coupled to the waveguide 24, a coaxial-to-waveguide converter 26 coupled to the isolator 25, and a coaxial cable 27 coupled to the coaxial-to-waveguide converter 26. The microwave oscillator 23 is also connected to the pulsed power source 29. Upon receiving power supplied from the pulsed power source 29, the microwave oscillator 23 oscillates a microwave.

The antenna 28 is connected to the coaxial cable 27. A tip end of the antenna 28 is pointed at a focal point of the light collection optical system 22. The microwave oscillated by the microwave oscillator 23 is radiated from the antenna 28 toward the focal point of the light collection optical system 22 via the microwave transmission paths 24 to 27.

As the microwave oscillator 23, for example, a magnetron that oscillates 2.45 GHz microwave may be employed. As the antenna 28, for example, a ¾ wavelength monopole antenna, which has a sufficient gain for the microwave oscillated by the microwave oscillator 23, may be employed. As the pulsed power source 29, for example, an inverter type power supply device may be employed.

The cavity 12 is an approximately cylindrical-shaped container having a resonance structure for the microwave and prevents the microwave from leaking outside. The cavity 12 is provided with a support member (not shown) that supports the target substance 15. The cavity 12 is provided with a light inlet window to let in the laser light oscillated by the laser light source 21. The laser light oscillated by the laser light source 21 is incident upon the cavity 12. Inside of the cavity 12, the target substance 15 turns into a plasma state due to the laser light. Also, inside of the cavity 12, the target substance 15 in the plasma state is irradiated with the microwave from the antenna 28.

Operation of Plasma Generation Device

The plasma generation device 11 performs a plasma generation and maintenance operation that turns the target substance 15 into a plasma state and maintains the target substance 15 in the plasma state in accordance with an instruction from the control device 14.

In the plasma generation and maintenance operation, the pulsed power source 29, upon receiving a start signal outputted from the control device 14, starts to supply power to the microwave oscillator 23. As a result thereof, the microwave oscillator 23 starts to oscillate microwaves, and the microwaves are radiated from the antenna 28 toward the target substance 15 in the cavity 12. In the cavity 12, the microwave resonates to form a standing wave. In the vicinity of a surface of the target substance 15 irradiated with the laser, an antinode of the standing wave is formed, and thus, a strong electric field region is generated.

Subsequently, the laser light source 21, upon receiving an oscillation signal outputted from the control device 14, oscillates a single pulse of laser light. The laser light is oscillated immediately after the microwave irradiation starts. The laser light oscillated by the laser light source 21 is condensed on the surface of the target substance 15 via the light collection optical system 22. A high density energy is momentarily applied to the target substance 15.

Figure 2:
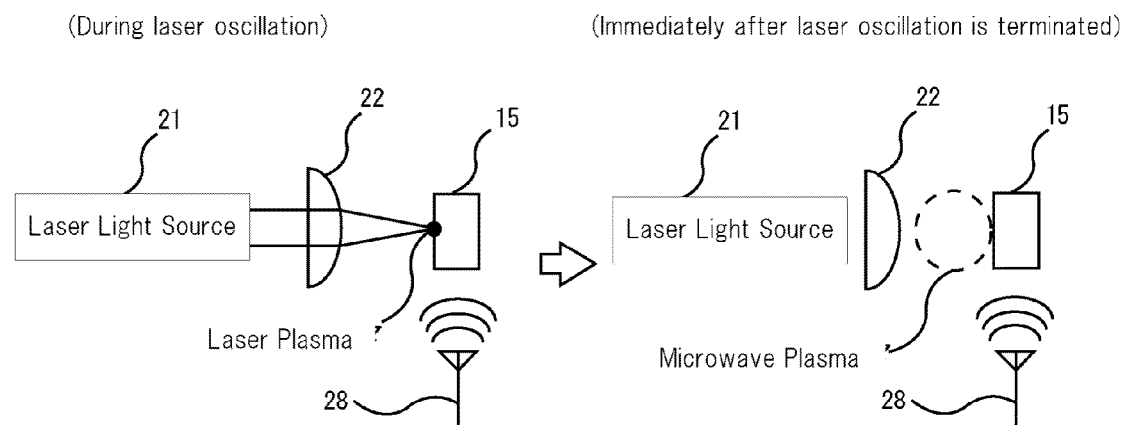
FIG. 2 is an explanatory diagram of a plasma generation and maintenance operation according to the first embodiment.

At a region irradiated with the laser light on the surface of the target substance 15, energy density increases and exceeds the breakdown threshold value of the target substance 15. Then, as shown in FIG. 2, substance at the region irradiated with the laser light is ionized and turned into a plasma state. This means that the plasma is generated out of the target substance 15 as raw material. Hereinafter, the plasma generated by the laser light is referred to as "laser plasma". The laser plasma corresponds to the initial plasma.

Immediately after the laser oscillation is terminated, the microwave irradiation is still continued. Therefore, as shown in FIG. 2, the laser plasma absorbs energy of the microwave and expands. The expanded plasma is maintained by the microwave. Hereinafter, the plasma maintained by the microwave is referred to as "microwave plasma". The microwave plasma corresponds to the electromagnetic wave plasma.

After that, the pulsed power source 29, upon receiving a termination signal outputted from the control device 14, stops supplying power to the microwave oscillator 23. As a result thereof, the microwave oscillator 23 terminates the microwave oscillation. The microwave oscillator 23 terminates after the laser light is oscillated. The microwave irradiation terminates, for example, 5 seconds after the laser light oscillation is terminated. Consequently, electron recombination occurs, and the microwave plasma vanishes.

The pulsed power source 29 repeatedly supplies pulse waves (or burst waves) to the microwave oscillator 23 from when the pulsed power source 29 receives the start signal until when the pulsed power source 29 receives the termination signal. The pulsed power source 29 supplies power to the microwave oscillator 23 at a predetermined duty cycle (duty ratio of on and off). The microwave oscillator 23 repeats oscillation and non-oscillation of the microwave at the predetermined duty cycle. The microwave plasma is maintained as non-equilibrium plasma without becoming thermal plasma. In the first embodiment, the microwave oscillation starts at a point of time when the first pulse wave is received and terminates at a point of time when the last pulse wave is received. The period from when the start signal is received until when the termination signal is received is defined as a microwave irradiation period. The microwave is maintained constant in energy per unit time during the microwave irradiation period without any adjustment.

Although, in the first embodiment, timing to start the microwave oscillation is set before the laser light is oscillated, the timing to start the microwave oscillation may be set after the laser light is oscillated as long as the microwave oscillation starts before the laser plasma vanishes.

Figure 3:
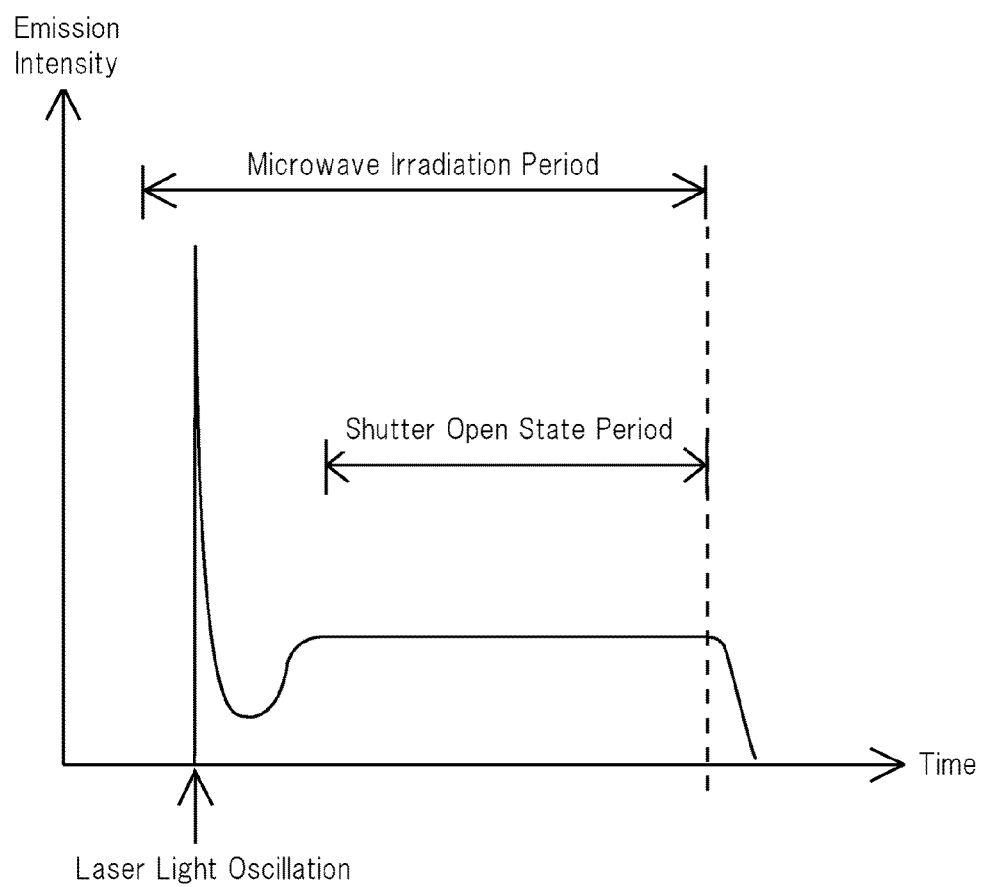
FIG. 3 is a graph showing time series variation in intensity of emission from plasma generated by a plasma generation device according to the first embodiment.

Here, as shown in FIG. 3, which illustrates time series variation in intensity of the plasma light emitted from the plasma while the plasma is being formed, firstly, a momentary peak of intensity of emission caused by the laser plasma occurs, and subsequently, the emission intensity drops to a minimum value, which is close to zero. After the emission intensity reaches the minimum value, the emission intensity increases again due to the microwave plasma, and then, maintains approximately at a constant value until the microwave plasma starts to vanish.

In the present specification, plasma formed until the emission intensity of the plasma reaches the minimum value immediately after the emission intensity of the plasma reaches the peak value due to the initial plasma is defined as the "laser plasma", and the plasma formed after the emission intensity of the plasma reaches the minimum value is defined as the "microwave plasma". In the first embodiment, the plasma generation device 11 is configured so that the laser plasma is higher in the maximum value of the emission intensity than the microwave plasma. The output powers of the laser light source 21 and the microwave oscillator 23 are configured so that the microwave plasma is higher in energy density than the laser plasma.

Construction of Optical Analysis Device

The optical analysis device 13 exclusively analyzes the plasma light emitted from the microwave plasma during the plasma generation and maintenance operation. The optical analysis device 13 constitutes an optical analysis unit that analyzes the target substance 15 based on time integral value of intensity of the emission from the electromagnetic wave plasma, which is maintained by the electromagnetic wave. The optical analysis device 13 includes a beam sampler 30, a first power meter 31A, a second power meter 31B, an optical element 32, an optical fiber 33, a spectrometer 34, an optical detector 35, and a signal processing device 36.

The beam sampler 30 is disposed between a laser light exit of the laser light source 21 and the light collection optical system 22. The beam sampler 30 separates a part of the laser light oscillated by the laser light source 21. The first power meter 31A receives the light separated by the beam sampler 30. An output signal from the first power meter 31A is inputted to the signal processing device 36. On the other hand, the second power meter 31B is disposed on an opposite side of the cavity 12 against the laser light source 21, and receives the laser light that has passed through the cavity 12. An output signal from the second power meter 31B is inputted to the signal processing device 36.

The optical element 32 is configured by a lens and the like which light can be transmitted through. As the optical element 32, for example, a light collection optical system is employed. In this case, the optical element 32 is disposed so that a focal point thereof is located at a region where the microwave plasma is formed.

The spectrometer 34 is connected to the optical element 32 via the optical fiber 33. The spectrometer 34 acquires the plasma light incident upon the optical element 32. The spectrometer 34 disperses the incident plasma light toward different directions according to wavelength by way of a diffraction grating or a prism.

The spectrometer 34 according to the first embodiment is provided at an entrance of the spectrometer 34 with a shutter 37 as an analysis period delimiting unit that delimits an analysis period for analyzing the plasma light so that the plasma light emitted from the microwave plasma can be exclusively analyzed while the plasma is being formed. The shutter 37 is switched by the control device 14 between an open state, in which light is allowed to be incident upon the spectrometer 34, and a closed state, in which light is not allowed to be incident upon the spectrometer 34. In a case in which the control device 14 can control exposure timing of the optical detector 35, the control device 14 may constitute the analysis period delimiting unit.

The optical detector 35 is disposed so as to receive light of a predetermined wavelength band from among the lights dispersed by the spectrometer 34. The optical detector 35, in response to an instruction signal outputted from the control device 14, converts the received light of the wavelength band into electrical signals according to wavelength and outputs them. As the optical detector 35, for example, a charge coupled device is employed. The electrical signals outputted from the optical detector 35 are inputted to the signal processing device 36.

Figure 4:
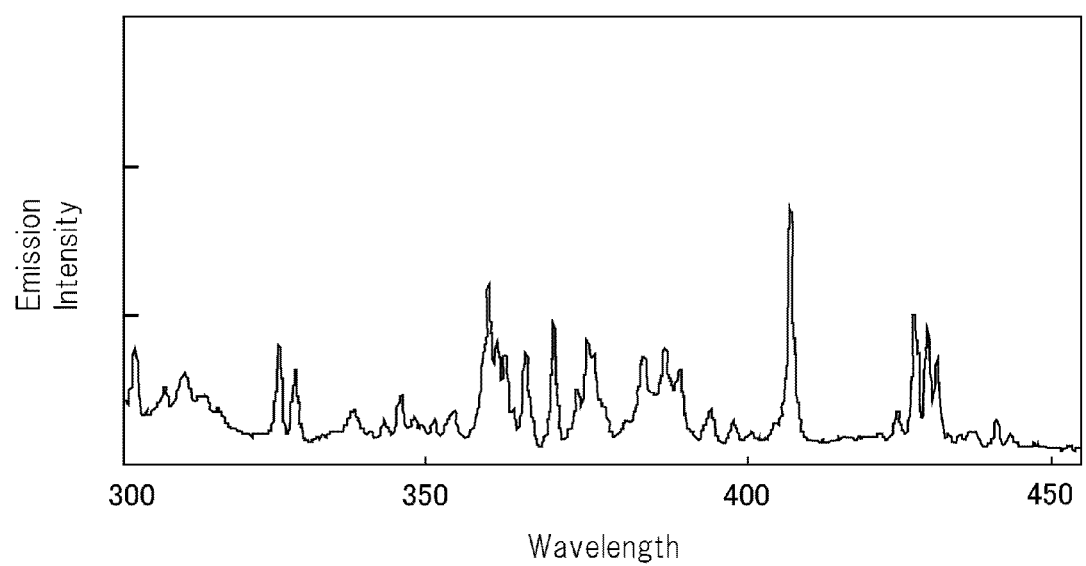
FIG. 4 is a spectrum showing time integral value of emission intensity according to wavelength for emission from plasma generated by the plasma generation device according to the first embodiment.

The signal processing device 36 calculates time integral values of intensity according to wavelength based on the electrical signals outputted from the optical detector 35. The signal processing device 36 acquires the time integral values of intensity according to wavelength (emission spectrum) for the plasma light incident upon the spectrometer 34 while the shutter 37 is in the open state. The signal processing device 36 generates information with respect to the time integral values of intensity according to wavelength as shown in the graph of FIG. 4. The signal processing device 36 identifies the target substance 15 by detecting a wavelength component having a high intensity based on the time integral values of intensity according to wavelength.

The signal processing device 36 detects energy of the laser light that has been oscillated by the laser light source 21 based on an output value from the first power meter 31A and a separation rate of the laser light by the beam sampler 30. The signal processing device 36 detects energy of the laser light that has passed through the cavity 12 based on an output value from the second power meter 31B. The signal processing device 36 detects energy that has been absorbed by the plasma based on a difference between the energy of the laser light that has passed through the cavity 12 and the energy of the laser light that has been oscillated by the laser light source 21.
Operation of Optical Analysis Device The optical analysis device 13 performs an optical analysis operation for analyzing the plasma light emitted from the plasma under instruction from the control device 14. The optical analysis operation is carried out in cooperation with the plasma generation and maintenance operation. In the plasma generation and maintenance operation, the shutter 37 is controlled by the control device 14 so as to be in the open state only while the microwave plasma is being formed.

More particularly, in the optical analysis device 13, during a period shown in FIG. 3 while the shutter 37 is in the open state, the plasma light emitted from the microwave plasma sequentially passes through the optical element 32 and the optical fiber 33 and is incident upon the spectrometer 34. The spectrometer 34 disperses the incident plasma light toward different directions according to wavelength. Thus, the plasma light of a predetermined wavelength band reaches the optical detector 35. The optical detector 35 converts the received plasma light of the wavelength band into electrical signals according to wavelength. The signal processing device 36 calculates the time integral values of intensity according to wavelength based on output signals from the optical detector 35. The signal processing device 36 identifies the target substance 15 by detecting a wavelength component having a high intensity based on the time integral values of intensity according to wavelength.

The signal processing device 36 may display on a monitor of the signal processing device 36 a graph showing the time integral values of intensity according to wavelength as shown in FIG. 4. A user of the analysis apparatus 10 can see the emission spectrum, thereby identifying atoms contained in the target substance 15 as component analysis of the target substance 15.

The analysis apparatus 10 may employ a calibration curve to calculate a content of the identified atom. In the case in which the content of the atom is calculated, the signal processing device 36 may correct the content of the atom acquired from the emission spectrum based on a detected value of the energy of the laser light that has been oscillated by the laser light source 21. The signal processing device 36 may correct the content of the atom acquired from the emission spectrum based on a detected value of the energy that has been absorbed by the plasma.

The analysis apparatus 10 according to the first embodiment can identify not only an atom but a molecule contained in the target substance 15 and can calculate a content of the molecule. In a case in which the target substance 15 is analyzed based on the plasma light emitted from the laser plasma, since energy density of the laser is too high, approximately entire molecules contained in the target substance 15 are decomposed into atoms. Therefore, emission from molecule is too weak, and it is impossible to detect a peak of intensity of the emission from the molecule. On the other hand, in the first embodiment, assuming that the emission from the microwave plasma contains emission from a molecule such as an OH radical, energy per unit time of the microwave radiated from the antenna 28 is adjusted to be equal to or less than a value at which a peak of intensity of the emission from the molecule can be detected. Accordingly, majority of the molecules can remain undecomposed in the microwave plasma, and it is possible to detect the peak of intensity of the emission from a molecule from the emission spectrum detected by the optical analysis device 13.

Effect of First Embodiment

In the first embodiment, the target substance 15 is analyzed based on time integral value of intensity of emission from the microwave plasma, duration of which is controllable. The microwave plasma can be maintained longer than plasma which is formed by a laser pulse alone. Accordingly, it is possible to acquire a large value of time integral of emission intensity, thereby enabling analysis at a high accuracy without using a high performance spectrometer.

Furthermore, in the first embodiment, since the plasma light from the microwave plasma contains emission from a molecule, and a peak of intensity of the emission from the molecule is detected, it is possible to realize the analysis apparatus 10 that can analyze molecules.

First Modified Example of First Embodiment

The analysis apparatus 10 according to a first modified example is an apparatus that analyzes gaseous substance or particulate substance contained in a fluid as the target substance. In the optical analysis device 13, in place of an optical element 32 that has a focal point thereof at the region where the microwave plasma is formed, an optical element 32 is employed that can acquire light emitted from a target region that is larger than a region where the laser plasma is formed. In this case, the spectrometer 34 acquires the plasma light emitted from the target region, and the optical analysis device 13 calculates the time integral value of intensity of emission from the target region. The calculated time integral value is employed for analyzing components of the target substance.

In the first modified example, since the plasma expands due to the microwave, the target substance can be analyzed based on the time integral value of intensity of emission from the region larger than the region where the laser plasma is formed. Therefore, it is possible to realize the analysis apparatus that can analyze a large region, in a case in which the target substance is gaseous substance or particulate substance contained in a fluid. This leads to the fact that it is possible to realize a highly reliable analysis in a case in which the target substance is gaseous substance or particulate substance contained in a fluid.

Second Modified Example of First Embodiment

In a second modified example, according to a phase state of the target substance, the microwave oscillated by the microwave oscillator 23 is adjusted in energy per unit time.

More particularly, the analysis apparatus 10 is provided with an input part for allowing the phase state of the target substance inputted therein. A user of the analysis apparatus 10 operates the input part according to the target substance 15. The analysis apparatus 10 sets a maximum voltage of the pulse wave outputted from the pulsed power source 29 according to an output signal of the input part. As a result thereof, the energy per unit time of the microwave oscillated by the microwave oscillator 23 is set to a value corresponding to the phase state of the target substance. For example, breakdown threshold is higher in solid state than in gaseous state. Therefore, the energy per unit time of the microwave is set higher for solid state than for gaseous state.

Furthermore, the irradiation duration, for which the microwave is oscillated by the microwave oscillator 23, may be adjusted according to the output signal from the input part. As a result thereof, the irradiation duration, for which the microwave is oscillated by the microwave oscillator 23, is adjusted in accordance with the phase state of the target substance.

Third Modified Example of First Embodiment

The analysis apparatus 10 according to the third modified example is configured so that a user can set an analysis time interval. As the analysis time interval is set shorter by the user, the microwave oscillated by the microwave oscillator 23 is adjusted higher in energy per unit time.

In the analysis apparatus 10, the plasma generation device 11 repeatedly performs generation and extinction of the plasma at an operation cycle, which is set to be equal to the inputted analysis time interval. The optical analysis device 13, in cooperation with the plasma generation device 11, analyzes components of the target substance based on the time integral value of intensity of the emission from the microwave plasma each time the plasma generation device 11 generates the plasma. Thus, in the analysis apparatus 10, an optical analysis operation is performed, which analyzes the target substance at each analysis time interval set by the user.

In the third modified example, the microwave is set higher in energy per unit time as the analysis time interval is set shorter so that the time integral value of intensity of the emission from the microwave plasma can maintain large enough even if the analysis time interval is reduced. Accordingly, it is possible to perform analysis at a high accuracy even if the analysis time interval is set shorter, i.e., the analysis apparatus 10 is set fast in time response.

Second Embodiment

A second embodiment is different from the first embodiment in the initial plasma generation unit.

Figure 5:
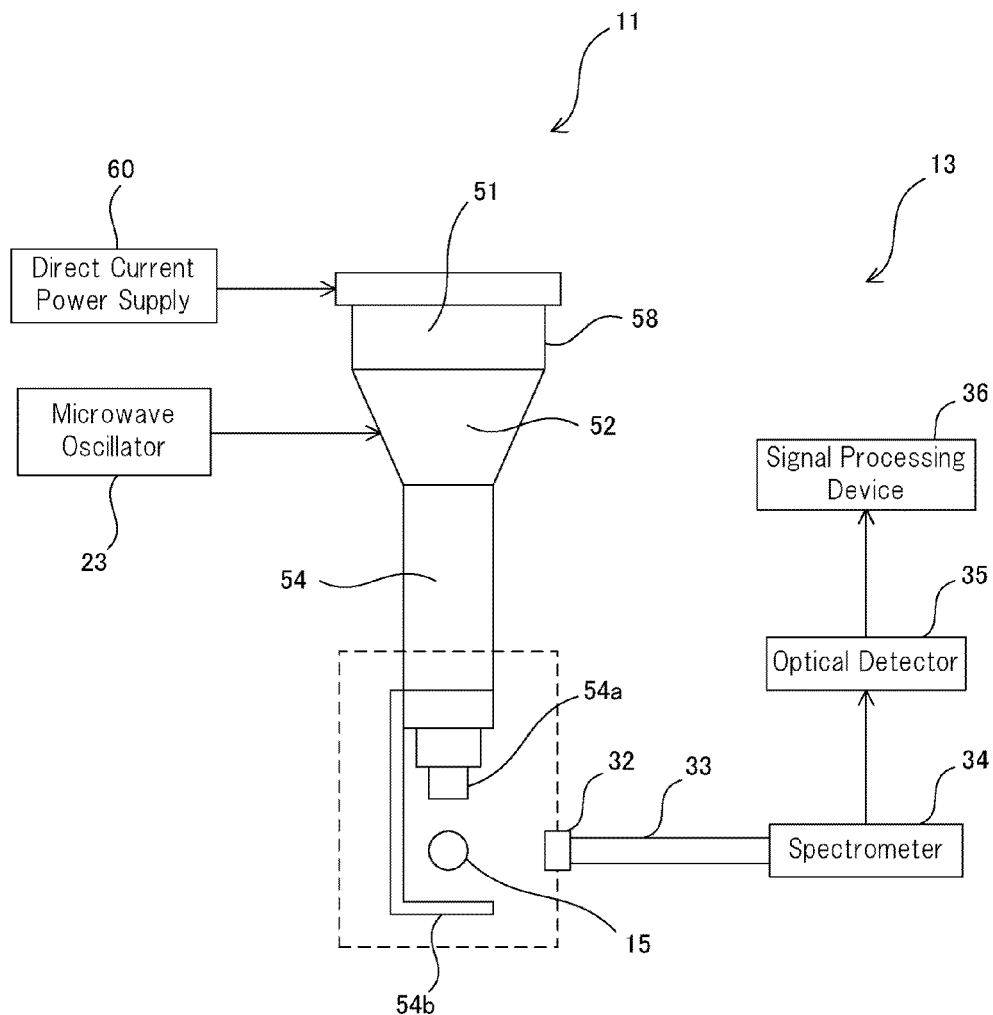
FIG. 5 is a schematic configuration diagram of an analysis apparatus according to a second embodiment.
Figure 6:
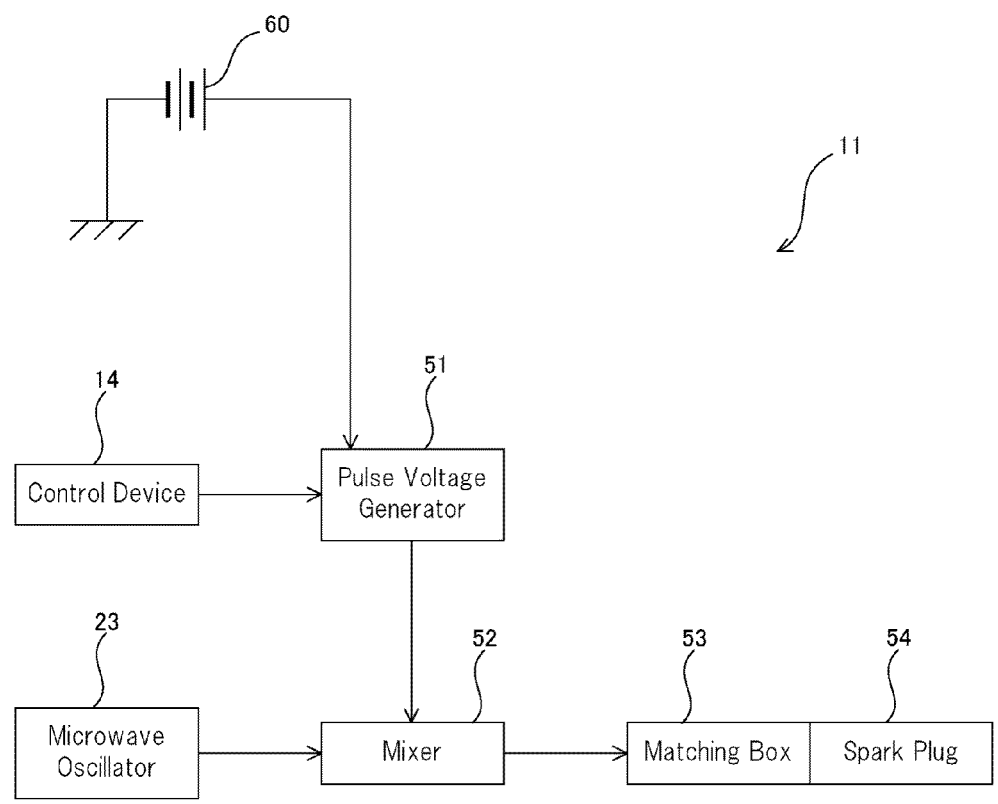
FIG. 6 is a schematic configuration diagram of a plasma generation device according to the second embodiment.

In the second embodiment, a discharge device (e.g., a spark plug) is employed to turn the target substance into a plasma state. More particularly, as shown in FIGS. 5 and 6, the plasma generation device 11 includes a pulse voltage generator 51, a microwave oscillator 23, a mixer 52, a matching box 53, and a spark plug 54. As shown in FIG. 5, the pulse voltage generator 51, the mixer 52, the matching box 53, and the spark plug 54 integrally constitute a discharge unit 58 (though the matching box 53 is not illustrated in FIG. 5).

The pulse voltage generator 51 is supplied with direct current power from a direct current power supply 60 provided outside thereof. The pulse voltage generator 51, upon receiving a discharge signal outputted from the control device 14, generates and outputs a high pulse voltage. The pulse voltage is a pulsed voltage signal having a peak voltage of 6 kV to 40 kV, for example. Properties of the pulse voltage may be configured as appropriate to the degree that the spark plug 54 can breakdown when the spark plug 54 is applied with the pulse voltage.

The mixer 52 receives the pulse voltage from the pulse voltage generator 51 as well as the microwave from the microwave oscillator 23. The mixer 52 generates and outputs a mixed signal of the pulse voltage and the microwave. The mixed signal is transmitted to the spark plug 54 via the matching box 53. The matching box 53 performs impedance matching of the microwave outputted from the mixer 52.

The spark plug 54 is formed with a discharge gap between a discharge electrode 54a and a ground electrode 54b. When the mixed signal is applied to the spark plug 54, a discharge occurs and a microwave is radiated. As a result thereof, small scale discharge plasma (initial plasma) is formed in the discharge gap at a tip end of the spark plug 54 caused by the discharge, and the discharge plasma absorbs energy of the microwave and expands. The expanded plasma becomes the microwave plasma. The microwave is radiated for a predetermined period of time.

Although, in the second embodiment, timing to start the microwave oscillation is set before the spark discharge, the timing may be set after the spark discharge as long as the microwave oscillation starts before the discharge plasma vanishes.

In the second embodiment, as shown in FIG. 5, the target substance 15 is disposed in the discharge gap. The target substance 15 is supported by a support member (not shown).

During the plasma generation and maintenance operation, light emitted from the target substance 15 in a plasma state is incident upon the optical element 32, which is disposed facing toward the target substance 15. Then, the optical analysis device 13 analyzes the target substance 15 similarly to the first embodiment.

Third Embodiment

Figure 7:
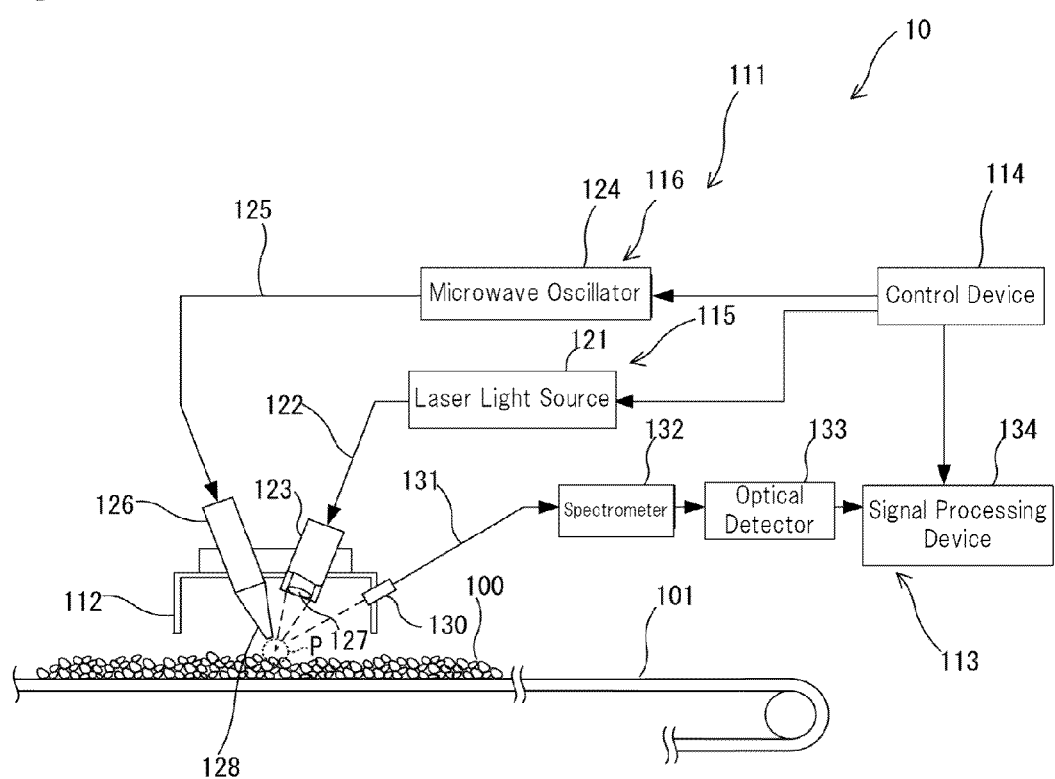
FIG. 7 is a schematic configuration diagram of an analysis apparatus according to a third embodiment.

An analysis apparatus 10 according to a third embodiment is an apparatus that analyzes powdery substance as the powdery substance 100. The analysis apparatus 10 can be utilized, for example, for detecting an impure substance. As shown in FIG. 7, The analysis apparatus 10 is disposed facing toward a belt conveyor 101 that transports the target substance 100. The analysis apparatus 10 is provided with a plasma generation device 111, a cavity 112, an optical analysis device 113, and a control device 114.

The cavity 112 is a container having a resonance structure for the microwave. The cavity 112 is formed in an approximately cylindrical shape open at a bottom side. The cavity 112 is configured by a mesh-shaped member. In the cavity 112, dimensions of the mesh are configured so that the microwave radiated toward inside of the cavity 112 from a radiation antenna 128, which will be described later, may not leak outside. A laser probe 123 and an antenna probe 126 are provided on a top surface of the cavity 112. The control device 114 controls the plasma generation device 111 and the optical analysis device 113.

Construction of Plasma Generation Device

The plasma generation device 111 constitutes a plasma generation unit that generates plasma in space, and maintains the plasma by energy of the microwave radiated from the radiation antenna 128. The plasma generation device 111 generates initial plasma by momentarily energizing a substance in space to be turned into a plasma state, and maintains the substance in the plasma state by irradiating the initial plasma with microwave for a predetermined period of time.

As shown in FIG. 7, the plasma generation device 111 is provided with a laser oscillation device 115 and an electromagnetic wave radiation device 116. The laser oscillation device 115 includes a laser light source 121, an optical fiber 122, and the laser probe 123. The electromagnetic wave radiation device 116 includes a microwave oscillator 124, a microwave transmission line 125, and the antenna probe 126.

The laser light source 121, upon receiving a laser oscillation signal from the control device 114, oscillates a laser light to generate the initial plasma. The laser light source 121 is connected to the laser probe 123 via the optical fiber 122. The laser probe 123 is provided at a tip end thereof with a light collection optical system 127 that collects the laser light that has passed through the optical fiber 122. The laser probe 123 is attached to the cavity 112 so that a tip end of the laser probe 123 faces toward inside of the cavity 112. A focal point of the light collection optical system 127 is located slightly below the bottom opening of the cavity 112. The laser light oscillated by the laser light source 121 passes through the light collection optical system 127 of the laser probe 123 and is condensed at the focal point of the light collection optical system 127.

As the laser light source 121, for example, a microchip laser may be employed. As the light collection optical system 127, for example, a convex lens may be employed.

The laser oscillation device 115 is configured so that energy density of the laser light condensed at the focal point of the light collection optical system 127 is not below a breakdown threshold value of the target substance 100. This means that the laser light source 121 is configured to have a sufficient power to turn the target substance 100 located at the focal point into plasma.

The microwave oscillator 124, upon receiving a microwave driving signal from the control device 114, continuously outputs a microwave for a period of the pulse width of the electromagnetic driving signal. The electromagnetic driving signal is a pulse signal having a constant voltage. The microwave oscillator 124 is configured so that the output power of the microwave from the microwave oscillator 124 does not exceed 100 W (for example, 80 W) in order to prevent the target substance 100 in a powdery state from scattering. The microwave oscillator 124 is connected to the antenna probe 126 via the microwave transmission line 125. The antenna probe 126 is provided with the radiation antenna 128 that radiates the microwave that has passed through the microwave transmission line 125. The radiation antenna 128 is attached to the antenna probe 126 so that a tip end of the radiation antenna 128 points at the focal point of the light collection optical system 127. The radiation antenna 128 is configured so that a strong electric field region formed by the microwave includes the focal point of the light collection optical system 127.

The microwave oscillator 124 outputs a microwave of 2.45 GHz. In the microwave oscillator 124, a semiconductor oscillator generates the microwave. A semiconductor oscillator that oscillates a microwave of another frequency band may be employed.

Construction of Optical Analysis Device

The optical analysis device 113 constitutes an optical analysis unit that analyzes the target substance 100 by analyzing plasma light emitted from the target substance 100 in plasma state located in a plasma region P during a plasma maintenance period, during which the plasma generation device 111 maintains the plasma by energy of the microwave. The optical analysis device 113 analyzes the target substance 100 based on a time integral value of intensity of the plasma light over an analysis period, which will be described later, within the plasma maintenance period. The optical analysis device 113 includes an optical probe 130, an optical fiber 131, a spectrometer 132, an optical detector 133, and a signal processing device 134.

The optical probe 130 is a device for guiding the plasma light from inside of the cavity 112. The optical probe 130 is configured by a cylindrical-shaped casing having a tip end, to which a lens is attached that can collect light from a relatively wide angle. The optical probe 130 is attached to a side surface of the cavity 112 in order to guide the plasma light emitted from the entire plasma region P to the lens.

The spectrometer 132 is connected to the optical probe 130 via the optical fiber 131. The spectrometer 132 acquires the plasma light incident upon the optical probe 130. The spectrometer 132 disperses the incident plasma light toward different directions according to wavelength by way of a diffraction grating or a prism.

The spectrometer 132 is provided at an entrance thereof with a shutter that delimits the analysis period for analyzing the plasma light. The shutter is switched by the control device 114 between an open state, in which light is allowed to be incident upon the spectrometer 132, and a closed state, in which light is not allowed to be incident upon the spectrometer 132. In a case in which exposure timing of the optical detector 133 is controllable, the analysis period may be delimited by controlling the optical detector 133.

The optical detector 133 is disposed so as to receive light of a predetermined wavelength band from among the light dispersed by the spectrometer 132. The optical detector 133, in response to an instruction signal outputted from the control device 114, converts the received light of the wavelength band into electrical signals according to wavelength and outputs them. As the optical detector 133, for example, a charge coupled device may be employed. The electrical signals outputted from the optical detector 133 are inputted to the signal processing device 134.

The signal processing device 134 calculates time integral values of intensity according to wavelength based on the electrical signals outputted from the optical detector 133. The signal processing device 134 calculates the time integral values of intensity according to wavelength (emission spectrum) for the plasma light incident upon the spectrometer 132 during the analysis period while the shutter is in the open state. The signal processing device 134 detects wavelength components having high intensities from the time integral values of intensity according to wavelength, thereby identifying the substances corresponding to the detected wavelength components, as components of the target substance 100.

Operation of Analysis Apparatus

The following description is directed to an analysis operation in which the analysis apparatus 10 performs component analysis of the target substance 100. The analysis operation is performed while the belt conveyor 101 is moving. In the analysis operation, a plasma generation and maintenance operation by the plasma generation device 111 and an optical analysis operation by the optical analysis device 113 are performed in cooperation with each other.

First, a description is given of the plasma generation and maintenance operation. The plasma generation and maintenance operation is an operation in which the plasma generation device 111 generates and maintains the plasma. The plasma generation device 111 performs the plasma generation and maintenance operation that generates the initial plasma by driving the laser light source 121, and irradiates the initial plasma with microwave by driving the microwave oscillator 124 to maintain the state of the plasma, under instruction from the control device 114.

More particularly, the control device 114 outputs the laser oscillation signal (a short pulse signal) to the laser light source 121. The laser light source 121, upon receiving the laser oscillation signal, oscillates a single pulse of laser light. The laser light oscillated by the laser light source 121 is condensed on a surface layer of the target substance 100 via the light collection optical system 127. A high density energy is momentarily applied to the target substance 100.

At a region irradiated with the laser light on the surface layer of the target substance 100, energy density increases and exceeds the breakdown threshold value of the target substance 100. Then, substance at the region irradiated with the laser light is ionized and turned into a plasma state. This means that plasma (initial plasma) is generated out of the target substance 100 as raw material.

Figure 8:
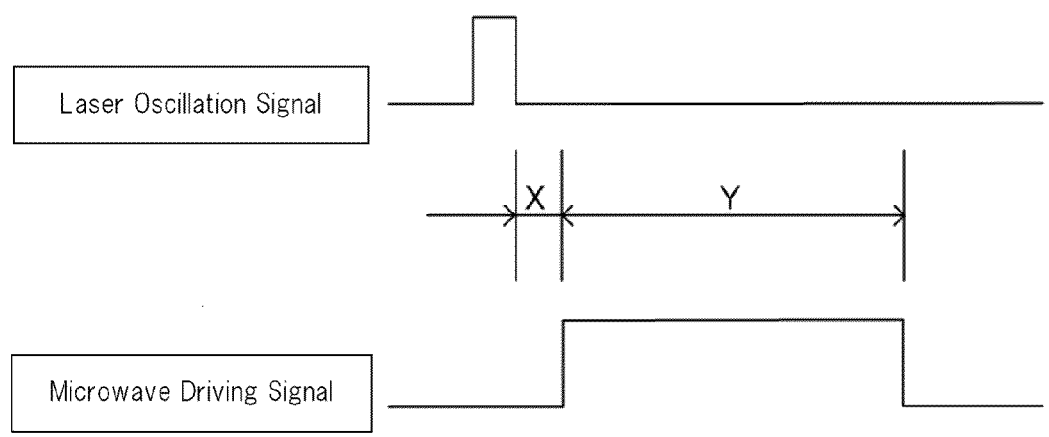
FIG. 8 is a time chart showing time relationship between a pulse oscillation signal and a electromagnetic driving signal according to the third embodiment.

Subsequently, as shown in FIG. 8, the control device 114 outputs the microwave driving signal to the microwave oscillator 124 immediately after a falling edge of the laser oscillation signal. The microwave oscillator 124, upon receiving the microwave driving signal, outputs a continuous wave (CW) of microwave to the radiation antenna 128. The microwave is radiated from the radiation antenna 128 toward an internal space of the cavity 112. The microwave is radiated from the radiation antenna 128 for a period of the pulse width of the electromagnetic driving signal. A time interval X from the falling edge of the laser oscillation signal until a rising edge of the microwave driving signal is set in such a manner that the microwave irradiation may start before the initial plasma vanishes.

In the internal space of the cavity 112, a strong electric field region (a region having a relatively strong electric field intensity within the internal space of the cavity 112) is formed centering on the focal point of the light collection optical system 127. The initial plasma absorbs the microwave energy, expands, and becomes microwave plasma in a spherical shape. In the internal space of the cavity 112, the plasma region P, where the microwave plasma is present, is formed in such a manner that the surface layer of the target substance 100 is included therein. The microwave plasma is maintained during a microwave irradiation period Y. The microwave irradiation period Y is defined as the plasma maintenance period.

After that, at a timing of a falling edge of the electromagnetic driving signal, the microwave oscillator 124 stops outputting the microwave, and the microwave plasma vanishes. The microwave irradiation period Y is, for example, tens of microseconds to tens of seconds. Even in a case in which the microwave is outputted for relatively long period, the microwave outputted from the microwave oscillator 124 is set to be a predetermined value (for example, 80 W) of output power so that the microwave plasma will not become thermal plasma.

Figure 9:
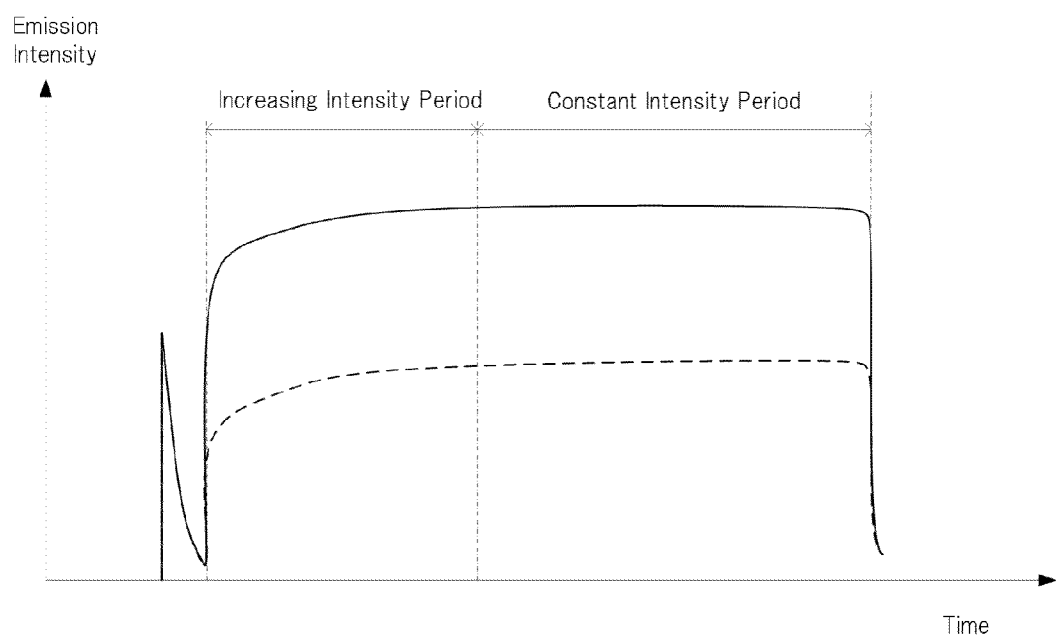
FIG. 9 is a graph showing time series variation in intensity of emission from plasma generated by a plasma generation device according to the third embodiment.

Here, as shown in FIG. 9, which illustrates time series variation in intensity of the plasma light emitted from the plasma during a period from generation of the initial plasma until extinction of the microwave plasma, firstly, a momentary peak of intensity of emission from the initial plasma occurs, and subsequently, the emission intensity drops to a minimum value, which is close to zero. After the emission intensity reaches the minimum value, an increasing intensity period, during which the emission from the microwave plasma increases in intensity, is observed. Following the increasing intensity period, a constant intensity period (a period during which variation (increase) in intensity of the plasma light is equal to or less than a predetermined value), during which the emission from the microwave plasma becomes constant in intensity, is observed.

In the plasma generation device 111 according to the third embodiment, as shown by a solid line in FIG. 9, power of the microwave during the plasma maintenance period is set in such a manner that a maximum value of intensity of the plasma light during the plasma maintenance period is higher than the time integral value of intensity of the plasma light before the microwave irradiation. As a result thereof, since the plasma light can have high intensity while preventing the target substance 100 from scattering, it is possible to analyze the target substance 100 more precisely. However, as shown in a dashed line in FIG. 9, the power of the microwave during the plasma maintenance period may be set in such a manner that the maximum value of intensity of the plasma light before the microwave radiation may be higher than the time integral value of intensity of the plasma light during the plasma maintenance period, as long as a sufficient emission intensity is available for such a configuration.

The optical analysis operation is an operation in which the optical analysis device 113 analyzes the emission (plasma light) from the target substance 100 in a plasma state. The optical analysis device 113 performs the optical analysis operation for analyzing components of the target substance 100 by spectroscopic analysis of the plasma light under instructions from the control device 114. In the optical analysis device 113, an analysis period is defined within a constant intensity period, in which intensity of the plasma light is approximately constant during the plasma maintenance period, and the target substance 100 is analyzed based on intensity of the plasma light during the analysis period. The control device 114 controls the shutter of the spectrometer 132 as well as a period of photoelectric conversion performed by the optical detector 133 so that the whole of the constant intensity period can be set as the analysis period. However, only a part of the constant intensity period may be set as the analysis period.

Meanwhile, when the initial plasma is generated, the target substance 100 scatters by a shock wave caused by the laser light. However, since the belt conveyor 101 is moving, the point where the target substance 100 scatters has already passed through the plasma region P at the start point of the constant intensity period. The target substance 100 located in the plasma region P at the start point of the constant intensity period has entered the plasma region P during the plasma maintenance period. The target substance 100 that has entered the plasma region P during the plasma maintenance period is not subject to influence of the scattering, but remains almost unmoved.

In the optical analysis device 113, exclusively during the constant intensity period (analysis period) shown in FIG. 9, the plasma light emitted from the target substance 100 in plasma state located in the plasma region P sequentially passes through the optical probe 130 and the optical fiber 131 and is incident upon the spectrometer 132.

The spectrometer 132 disperses the incident plasma light toward different directions according to wavelength, and the plasma light of the predetermined wavelength band reaches the optical detector 133. The optical detector 133 photoelectrically converts the received plasma light of the wavelength band into electrical signals according to wavelength. The signal processing device 134 calculates time integral values of intensity of emission during the constant intensity period (analysis period) according to wavelength based on output signals from the optical detector 133. The signal processing device 134 outputs a spectrum showing the time integral values of intensity according to wavelength as shown in FIG. 4. The signal processing device 134 detects a wavelength where a peak of intensity occurs from among the time integral values according to wavelength, and identifies the substance (atom or molecule) corresponding to the detected wavelength as a component of the target substance 100.

In the signal processing device 134, for example, when a peak of intensity is found at 379.4 nm, molybdenum is identified as a component of the target substance 100. For example, when a peak of intensity is found at 422.7 nm, calcium is identified as a component of the target substance 100. For example, when a peak of intensity is found at 345.2 nm, cobalt is identified as a component of the target substance 100. For example, when a peak of intensity is found at 357.6 nm, chromium is identified as a component of the target substance 100.

The signal processing device 134 may display a spectrum as shown in FIG. 4 on a monitor of the analysis apparatus 10. A user of the analysis apparatus 10 can identify components contained in the target substance 100 by observing the spectrum.

Effect of Third Embodiment

In the third embodiment, since the microwave stably energizes the plasma region P during the plasma maintenance period, occurrence of a shock wave caused by the microwave is prevented. The analysis period, during which the optical analysis device 113 performs analysis, is within the plasma maintenance period. Accordingly, in a case in which the target substance 100 is powdery substance, it is possible to prevent the target substance 100 in the plasma region P from scattering during the analysis period. This means that it is possible to analyze the target substance 100 in a state in which the target substance 100 remains almost unmoved in the plasma region P.

Furthermore, in the third embodiment, it is possible to analyze a powdery substance as it is. Conventionally, in a case in which a powdery substance is subject to analysis, the powdery substance has been solidified using a binder, and the resultant pellet has been analyzed. However, in the third embodiment, since the powdery substance can be analyzed as it is, no noise appears in emission intensity caused by the binder. Therefore, it is possible to omit a filter for removing the noise.

Furthermore, in the third embodiment, the microwave plasma is not extremely strong during the plasma maintenance period. Accordingly, constituent metal of the radiation antenna 128 is hardly excited, and it is possible to prevent a noise due caused by the metal.

First Modified Example of Third Embodiment

In a first modified example, the signal processing device 134 detects mixture ratio of a plurality of components in the target substance 100. The plasma maintained by the plasma generation device 111 of the third embodiment is greater than the plasma generated by the laser light alone. Therefore, the plasma light can be acquired from a larger region, thereby enabling detection of the mixture ratio of components in the region.

The signal processing device 134 stores data of calibration lines indicative of relationship between emission intensity and content for a plurality of substances. The signal processing device 134 detects a plurality of substances corresponding to wavelengths at which peak intensity occurs, and calculates content of each detected substance based on the data of calibration lines. The signal processing device 134 calculates content ratios of substances corresponding to wavelengths at which peak intensity occurs, thereby detecting mixture ratios of components contained in the target substance 100.

According to the first modified example, for example, in a case in which the analysis apparatus 10 is applied to quality control of medicines, it is possible to detect whether or not a mixture ratio between specific components in a medicine falls within a predetermined range. For example, the signal processing device 134 calculates respective contents of components A and B based on respective emission intensities at peak wavelengths corresponding to the components A and B contained in a powdered medicine. Based on the contents of the components A and B, the signal processing device 134 calculates the mixture ratio (content ratio by weight) of the component B to the component A.

The signal processing device 134 may correct the content of the substance acquired from the intensity spectrum based on reflection wave energy of microwave at the radiation antenna 128 of the electromagnetic wave radiation device 116. As the reflection wave energy increases, the energy of the microwave used for maintaining the microwave plasma decreases, and intensity of the plasma light decreases. The signal processing device 134 performs correction by increasing the content of the substance acquired from the intensity spectrum in proportion to the increase in the reflection wave energy of microwave.

Second Modified Example of Third Embodiment

In a second modified example, the optical analysis device 113 analyzes the plasma light during the plasma maintenance period, thereby detecting gas temperature in the plasma region P.

Fourth Embodiment

A fourth embodiment is different from the third embodiment in the initial plasma generation unit.

Figure 10:
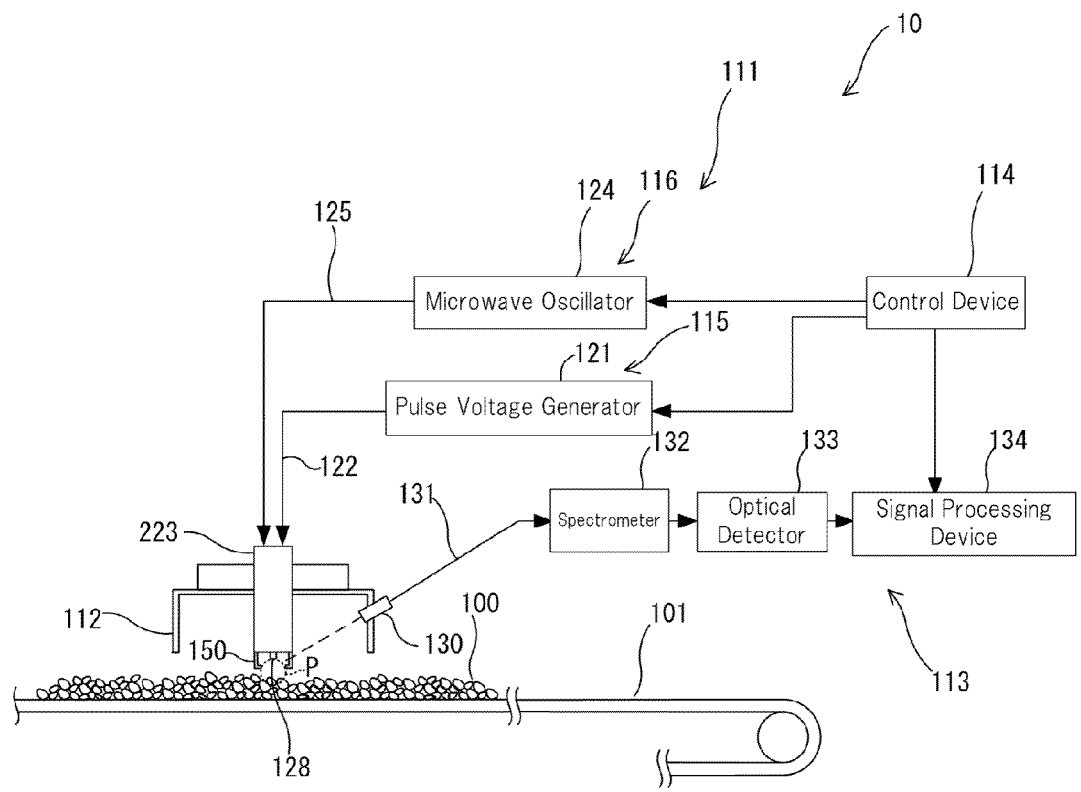
FIG. 10 is a schematic configuration diagram of an analysis apparatus according to a fourth embodiment.

In the fourth embodiment, as shown in FIG. 10, a spark plug 223 (discharge device) is employed to generate the initial plasma. When the initial plasma is to be generated, the control device 114 outputs a spark generation signal to a pulse voltage generator 121. The pulse voltage generator 121 outputs a high voltage pulse to the spark plug 223, thereby generating a spark discharge at a discharge gap between electrodes 150 of the spark plug 223. The initial plasma is generated at a path of the spark discharge. The high voltage pulse is a pulsed voltage signal having a peak voltage of 6 kV to 40 kV, for example.

In the fourth embodiment, a radiation antenna 128 is embedded in the spark plug 223. The control device 114 outputs a microwave driving signal to the microwave oscillator 124 immediately after the falling edge of the spark generation signal. The microwave oscillator 124 outputs a continuous wave of microwave from the radiation antenna 128, similarly to the third embodiment. As a result thereof, the initial plasma generated by the spark discharge absorbs energy of the microwave and expands. The radiation antenna 128 may be provided separately from the spark plug 223.

Other Embodiments

The above described embodiments may also be configured as follows.

In the embodiments described above, the time integral value of intensity used for the analysis of the target substance 15 is a time integral value of intensity exclusively over a period when the emission from the microwave plasma is maintained constant in intensity. However, the time integral value may include an integral value of intensity over a period when the emission from the microwave plasma increases in intensity (increasing period of intensity after the emission intensity reaches the minimum value following the peak of intensity of the emission caused by the laser plasma), and may include an integral value of intensity over a period when the emission decreases in intensity while the microwave plasma is vanishing.

In the embodiments described above, as the laser light source 21, a solid state laser light source other than Nd:YAG laser light source may be employed. Also, a liquid laser light source, a gas laser light source, a semiconductor laser light source, or a free electron laser light source may be employed.

Furthermore, in the embodiments described above, the unit for causing breakdown (the initial plasma generation unit) may suffice as long as it can provide sufficient energy to cause breakdown, and may be a thermal electron generator such as glow plug, a laser diode, or a super luminosity LED other than the laser light source 21 and the spark plug 54.

Furthermore, in the embodiments described above, as the microwave oscillator 23, other types of oscillator such as a semiconductor oscillator may be employed.

INDUSTRIAL APPLICABILITY

The present invention is applicable to an analysis apparatus and an analysis method for analyzing a target substance by analyzing emission from plasma.

Explanation of Reference Numerals

10 Analysis Apparatus
11 Plasma Generation Device (Plasma Generation Unit)
12 Cavity
13 Optical Analysis Device (Optical Analysis Unit)
21 Laser Light Source
22 Light Collection Optical System
23 Microwave Oscillator
28 Antenna
32 Optical Element
33 Optical Fiber

The invention claimed is:

1. An analysis apparatus, comprising: a plasma generation unit that generates initial plasma by energizing a substance in space to be turned into a plasma state, and maintains the substance in the plasma state by irradiating the initial plasma with electromagnetic wave for a predetermined period of time; and an optical analysis unit that analyzes a target substance based on time integral value of intensity of emission from the target substance in an electromagnetic wave plasma region, which is maintained by the electromagnetic wave,
wherein the plasma generation unit repeats generation and extinction of the plasma at a predetermined operation cycle, and the optical analysis unit analyzes the target substance based on the time integral value of intensity of the emission from the electromagnetic wave plasma each time the plasma generation unit generates plasma, and wherein the electromagnetic wave radiated by the plasma generation unit is increased in energy per unit time in proportion to a decrease in the operation cycle.

2. The analysis apparatus according to claim 1, wherein the plasma generation unit radiates the electromagnetic wave in continuous wave form from a radiation antenna provided in a space where the initial plasma is generated during a plasma maintenance period, during which the plasma generation unit maintains the plasma.

3. The analysis apparatus according to claim 2, wherein the target substance is moved in the electromagnetic wave plasma region during the plasma maintenance period.

4. The analysis apparatus according to claim 2, wherein the plasma generation unit, upon receiving a pulse signal of constant voltage, radiates the electromagnetic wave from the radiation antenna, and the optical analysis unit sets an analysis period in a constant intensity period, in which variation in intensity of emission from the plasma is equal to or less than a predetermined value, within the plasma maintenance period, and analyzes the target substance based on intensity of the emission from the plasma during the analysis period.

5. The analysis apparatus according to claim 2, wherein the target substance is powdery substance, and, the plasma generation unit sets power of the electromagnetic wave during the plasma maintenance period to the degree that the target substance may not scatter.

6. The analysis apparatus according to claim 5, wherein, the plasma generation unit sets power of the electromagnetic wave during the plasma maintenance period to the degree that a maximum value of intensity of emission from the plasma during the plasma maintenance period is greater than the time integral value of intensity of emission from the initial plasma.

7. The analysis apparatus according to claim 2, wherein the optical analysis unit analyzes the emission from the plasma during the plasma maintenance period, thereby detecting mixture ratios of components contained in the target substance.

8. The analysis apparatus according to claim 2, wherein the optical analysis unit analyzes the emission from the plasma during the plasma maintenance period, thereby detecting a temperature of gas in the electromagnetic wave plasma region.

* * * * *